(12) United States Patent
Heim-Riether et al.

(10) Patent No.: US 8,338,367 B2
(45) Date of Patent: Dec. 25, 2012

(54) FUSED HETEROARYL DIAMIDE COMPOUNDS USEFUL AS MMP-13 INHIBITORS

(75) Inventors: Alexander Heim-Riether, Biberach an der Riss (DE); Shuang Liang, Danbury, CT (US); Sabine Schlyer, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/123,002

(22) PCT Filed: Oct. 13, 2009

(86) PCT No.: PCT/US2009/060439
§ 371 (c)(1),
(2), (4) Date: Jul. 11, 2011

(87) PCT Pub. No.: WO2010/045190
PCT Pub. Date: Apr. 22, 2010

(65) Prior Publication Data
US 2011/0269668 A1    Nov. 3, 2011

Related U.S. Application Data

(60) Provisional application No. 61/105,455, filed on Oct. 15, 2008.

(51) Int. Cl.
*A61K 38/00* (2006.01)
*A61K 38/48* (2006.01)
*A61K 38/55* (2006.01)
*A61K 31/44* (2006.01)
*C07K 14/47* (2006.01)
*C07K 14/81* (2006.01)
*A61P 9/10* (2006.01)
*A61P 9/00* (2006.01)
*A61P 19/02* (2006.01)
*A61P 29/00* (2006.01)
*A61P 19/10* (2006.01)
*A61P 35/00* (2006.01)
*A01N 43/42* (2006.01)

(52) U.S. Cl. ...... 514/1.9; 514/16.4; 514/16.6; 514/16.8; 514/16.9; 514/19.4; 514/20.1; 514/279

(58) Field of Classification Search ............... None
See application file for complete search history.

(56) References Cited

U.S. PATENT DOCUMENTS

| 2002/0165222 A1 | 11/2002 | Marquis et al. |
| 2004/0063686 A1 | 4/2004 | Johnson et al. |
| 2005/0004111 A1 * | 1/2005 | Klingler et al. ............ 514/227.5 |
| 2005/0203127 A1 | 9/2005 | Cezanne et al. |
| 2007/0213333 A1 | 9/2007 | Shoda et al. |
| 2008/0039442 A1 | 2/2008 | Blom et al. |

FOREIGN PATENT DOCUMENTS

| WO | 0033836 A1 | 6/2000 |
| WO | 0055126 A2 | 9/2000 |
| WO | 0210146 A1 | 2/2002 |
| WO | 0216348 A1 | 2/2002 |
| WO | 2006008133 A2 | 1/2006 |
| WO | 2006086705 A1 | 8/2006 |
| WO | 2007024600 A2 | 3/2007 |
| WO | 2010045188 A1 | 4/2010 |
| WO | 2010045190 A1 | 4/2010 |
| WO | 2010056585 A2 | 5/2010 |

OTHER PUBLICATIONS

Shah et al, An MMP13-selective inhibitor delays primary tumor growth and the onset of tumor-associated osteolytic lesions in experimental models of breast cancer, PLoS One. 2012;7(1):e29615.*
International Search Report and Written Opinion for PCT/US2009/060439 mailed Dec. 17, 2009.

* cited by examiner

*Primary Examiner* — Anish Gupta
*Assistant Examiner* — Sergio Coffa
(74) *Attorney, Agent, or Firm* — Michael P. Morris; Anthony P. Bottino

(57) ABSTRACT

Disclosed are compounds and compositions of the formula I as described herein which are inhibitors of MMP-13. Also disclosed are methods of using and making compounds of the formula I.

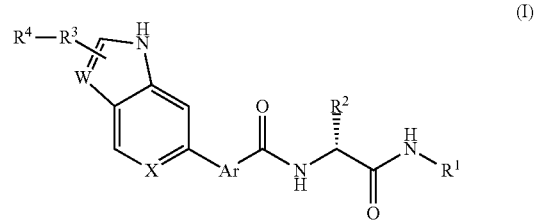

9 Claims, No Drawings

FUSED HETEROARYL DIAMIDE COMPOUNDS USEFUL AS MMP-13 INHIBITORS

APPLICATION DATA

This application claims benefit to U.S. provisional application Ser. No. 61/105,455 filed Oct. 15, 2008.

BACKGROUND OF THE INVENTION

1. Technical Field

The invention relates to MMP-13 metalloprotease inhibiting compounds.

2. Background Information

Matrix metalloproteinases (MMPs) are zinc-dependent endopeptidases. MMPs function to degrade extracellular matrix proteins and are involved in the cleavage of cell surface receptors, growth factors, cell-adhesion molecules, cytokines and chemokines, as well as other MMPs and unrelated proteases. MMPs are also thought to play a major role on cellular processes such as proliferation, migration (adhesion/dispersion), differentiation, angiogenesis, apoptosis and host defense. (Hu J et al. Nat Rev Drug Discov. 2007 6:480-498; Ramnath N and Creaven P J Curr Oncol Rep. 2004 6:96-102). MMPs are therefore targets for therapeutic diseases including rheumatoid arthritis, osteoarthritis, osteoporosis, peridontitis, atherosclerosis, congestive heart failure, multiple sclerosis and tumor metastasis.

The mammalian MMP family includes more than 20 members that share common structural attributes: a propeptide domain, a catalytic domain and a C-terminal hemopexin-like domain (except for MMP-7 and MMP-26). The function of MMPs in health and disease is regulated in multiple ways. MMPs are secreted as inactive proproteins which are activated when the propepetide domain is cleaved by extracellular proteinases or destabilized by protein-protein interactions. The activity of MMPs is also regulated by tissue inhibitors of metalloproteinases (TIMPs) which bind to the catalytic site of MMPs. The production of MMPs is also regulated at the level of transcription by specific signals that are temporally limited and spatially confined. (Parks W C et al 2004, Nat Rev Immunol. 2004 4:617-629).

The collagenase subset of the matrix metalloproteinase family, comprising MMP-1 (collagenase 1), MMP-8 (collagenase 2), MMP-13 (collagenase 3) and more recently MMP-14, catalyzes the initial cleavage of collagen types I, II, III, V and X (Parks W C et al 2004, Nat Rev Immunol. 2004 4:617-629). MMP-13 cleaves type II collagen more efficiently than types I and III and is capable of cleaving multiple extracellular matrix proteins in addition to fibrillar collagens (Leeman M F et al 2003 Crit. Rev. Biochem. Mol. Biol. 37: 149-166). MMP-13 is the most proficient catalyst of collagen type II degradation, the committed step in articular cartilage degradation and progressive joint damage associated with RA and osteoarthritis (OA). In the case of collagen type II (90-95% of articular cartilage), the triple helix is cleaved at position G775/L776 at least an order of magnitude faster by MMP-13 than by MMP-1 and MMP-8 (Billinghurst, R. C. et al. 1997 J Clin Invest 99, 1534-1545). Cleavage of collagen type II triple helix at position G775/L776 by MMP-13 triggers the initial unfolding of the molecule, rendering it susceptible to catalytic degradation by additional members of the MMP family. The superior catalytic efficiency of MMP-13 for collagen type II degradation, coupled with induced expression of MMP-13 in synovial fibroblasts and chondrocytes associated with rheumatoid arthritis (RA) and osteoarthritis (OA) pathology, is consistent with MMP-13 being responsible for catalyzing the committed step in cartilage degradation associated with RA and OA (Mitchell, P. G. et al. 1996 J Clin Invest 97, 761-768; Moore, B. A. et al, 2000 Biochim. Biophys. Acta 1502, 307-318).

Furthermore, transient adenoviral expression of MMP-13 in mouse knee chondrocytes and synoviocytes induces a transient arthritic condition, including recruitment of inflammatory cells, and up-regulation of inflammatory cytokine mRNA (oronen, K. et al. 2004. Ann Rheum. Dis 63, 656-664). Transgenic mice with a constitutively active form of human MMP-13 in cartilage exhibit augmented cleavage of type II collagen and leading to an osteoarthritic-like phenotype with marked cartilage degradation and synovial hyperplasia (Neuhold, L. A. et al 2001 J Clin Invest 107, 35-44). These in vivo validation studies further support the role of MMP-13 in RA and OA pathogenesis.

BRIEF SUMMARY OF THE INVENTION

It has been found that compounds of the present invention are inhibitors of MMP-13.

It is therefore an object of the invention to provide compounds and compositions of the formula I as described herein below which are inhibitors of MMP-13.

It is a further object of the invention to provide methods of using and making compounds of the formula I which are inhibitors of MMP-13.

DETAILED DESCRIPTION OF THE INVENTION

In the broadest generic embodiment, there is provided a compound of the formula (I):

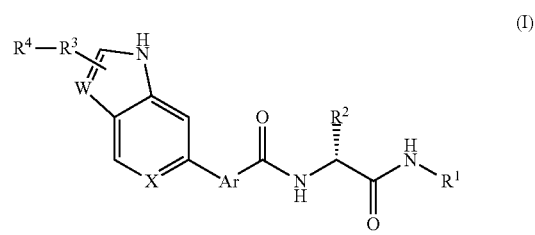

wherein:
$R^1$ is $C_1$-$C_5$ alkyl optionally substituted with 1-2 substituents chosen from hydroxyl, $C_1$-$C_5$ alkoxy, aryl and heteroaryl;
$R^2$ is $C_1$-$C_5$ alkyl, carbocycle, heterocycle or heteroaryl, each optionally independently substituted with 1-2 substituents chosen from amino, hydroxyl and $C_1$-$C_5$ alkoxy;
$R^3$ is a bond, —$(CH_2)_n$—, —C(O)—, O, NH or —S(O)$_m$—;
$R^4$ is hydrogen, $C_1$-$C_5$ alkyl, amino, alkylamino, dialkylamino, heterocyclyl or heteroaryl, each optionally independently substituted with 1-3 substituents chosen from $C_1$-$C_5$ alkyl, acyl, halogen, hydroxyl, oxo and $C_1$-$C_5$ alkoxy;
W is N, O or CH wherein CH is optionally substituted with halogen, $C_1$-$C_5$ alkyl, $C_1$-$C_5$ alkoxy or —C(O)—$NH_2$ wherein the nitrogen atom is optionally mono or di substituted with a $C_1$-$C_3$ alkyl group;
X is N or CH;
Ar is a heteroaryl ring chosen from furanyl, thiazolyl, pyrazolyl, imidazolyl, pyrrolyl, pyridinyl, pyrimidinyl, pyridazinyl and quinolinyl;
each m, n is 0-2;
wherein each $R^1$-$R^4$ is optionally partially or fully halogenated;
or a pharmaceutically acceptable salt thereof.

In another embodiment, there is provided a compound of the formula (I) according the embodiment described immediately above, and wherein $R^1$ is $C_1$-$C_5$ alkyl optionally substituted with 1-2 substituents chosen from hydroxyl and $C_1$-$C_5$ alkoxy;

$R^2$ is $C_1$-$C_5$ alkyl, cyclobutyl, cyclopentyl, cyclohexyl, tetrahydropyranyl, piperidinyl or piperazinyl, each optionally independently substituted with 1-2 substituents chosen from amino, hydroxyl and $C_1$-$C_5$ alkoxy;

$R^3$ is a bond, $CH_2$, O, NH, —C(O)—, —S(O)$_m$— or —SO$_2$—;

$R^4$ is hydrogen, $C_1$-$C_5$ alkyl, amino, alkylamino, dialkylamino, morpholinyl, thiomorpholinyl, 1,1-dioxo-1$\lambda^6$-thiomorpholinyl, piperazinyl, piperidinyl, pyrazolyl, imidazolyl, pyrrolyl, pyrrolidinyl or pyridinyl, each optionally independently substituted with 1-3 substituents chosen from $C_1$-$C_5$ alkyl, acyl, halogen, hydroxyl, oxo and $C_1$-$C_5$ alkoxy;

W is N, O or CH;

X is N or CH;

Ar is a heteroaryl ring chosen from furanyl, thiazolyl, pyrazolyl, imidazolyl, pyrrolyl, pyridinyl, pyrimidinyl and pyridazinyl.

In another embodiment, there is provided a compound of the formula (I) according the embodiment described immediately above, and wherein $R^1$ is $C_1$-$C_5$ alkyl;

$R^2$ is $C_1$-$C_5$ alkyl or cyclohexyl;

$R^3$ is $CH_2$ or —C(O)—;

$R^4$ is hydrogen, morpholinyl, thiomorpholinyl, 1,1-dioxo-1$\lambda^6$-thiomorpholinyl, piperazinyl, piperidinyl, pyrazolyl or pyridinyl, each optionally independently substituted with 1-3 substituents $C_1$-$C_5$ alkyl;

W is N or CH;

Ar is furanyl.

In another embodiment, there is provided a compound of the formula (I) according the embodiment described immediately above, and wherein $R^1$ is methyl;

$R^2$ is isopropyl or cyclohexyl;

$R^3$ is $CH_2$ or —C(O)—;

$R^4$ is hydrogen, morpholinyl or pyridinyl, each optionally substituted with 1-3 methyl groups.

In another embodiment, there is provided a compound of the formula (I) according the first generic embodiment, wherein X is CH.

In another embodiment, there is provided a compound of the formula (I) according the first generic embodiment, wherein X is N.

In another embodiment, the invention provides compounds in Table I which can be made in view of the general schemes, examples and methods known in the art.

TABLE I

| Structure | Name |
|---|---|
| 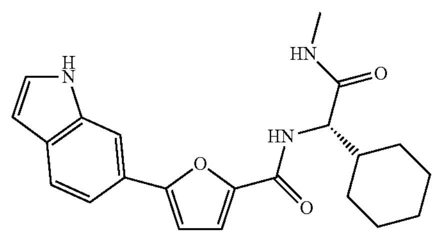 | 5-(1H-Indol-6-yl)-furan-2-carboxylic acid ((S)-cyclohexyl-methylcarbamoyl-methyl)-amide |
| 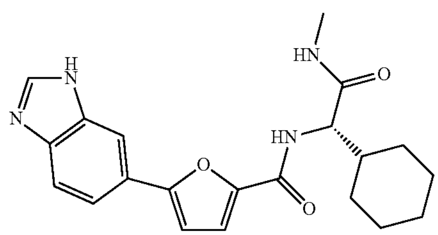 | 5-(3H-Benzimidazol-5-yl)-furan-2-carboxylic acid ((S)-cyclohexyl-methylcarbamoyl-methyl)-amide |
| 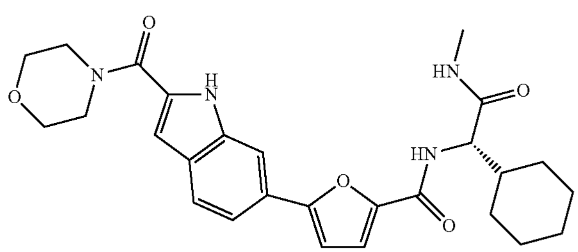 | 5-[2-(Morpholine-4-carbonyl)-1H-indol-6-yl]-furan-2-carboxylic acid ((S)-cyclohexyl-methylcarbamoyl-methyl)-amide |

TABLE I-continued

| Structure | Name |
|---|---|
| 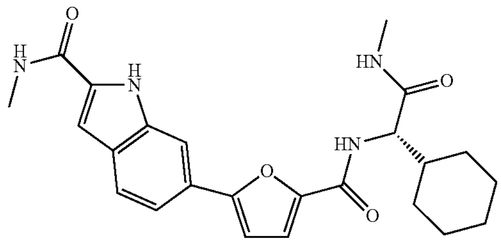 | 6-{5-[((S)-Cyclohexyl-methylcarbamoyl-methyl)-carbamoyl]-furan-2-yl}-1H-indole-2-carboxylic acid methylamide |
| 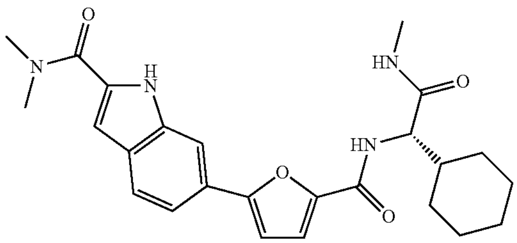 | 6-{5-[((S)-Cyclohexyl-methylcarbamoyl-methyl)-carbamoyl]-furan-2-yl}-1H-indole-2-carboxylic acid dimethylamide |
| 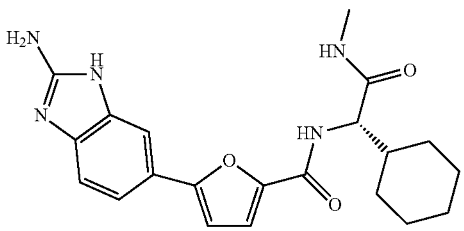 | 5-(2-Amino-3H-benzimidazol-5-yl)-furan-2-carboxylic acid ((S)-cyclohexyl-methylcarbamoyl-methyl)-amide |
| 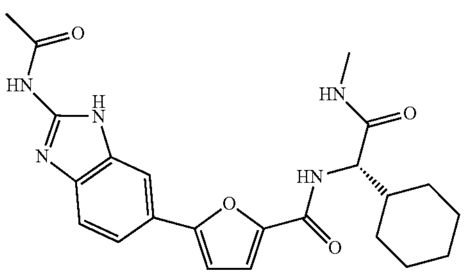 | 5-(2-Acetylamino-3H-benzimidazol-5-yl)-2-carboxylic acid ((S)-cyclohexyl-methylcarbamoyl-methyl)-amide |
| 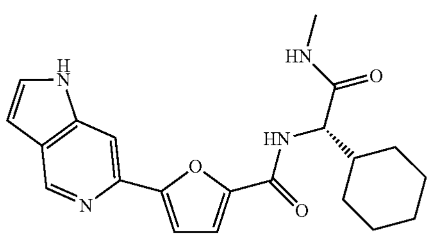 | 5-(1H-Pyrrolo[3,2-c]pyridin-6-yl)-furan-2-carboxylic acid ((S)-cyclohexyl-methylcarbamoyl-methyl)-amide |
| 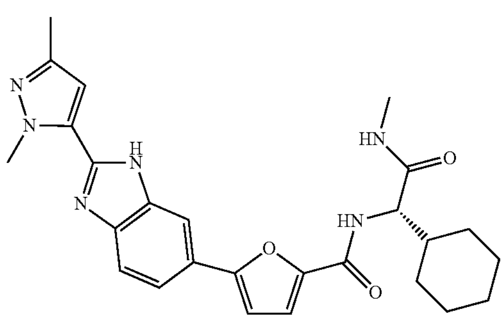 | 5-[2-(2,5-Dimethyl-2H-pyrazol-3-yl)-3H-benzimidazol-5-yl]-furan-2-carboxylic acid ((S)-cyclohexyl-methylcarbamoyl-methyl)-amide |

TABLE I-continued

| Structure | Name |
|---|---|
| 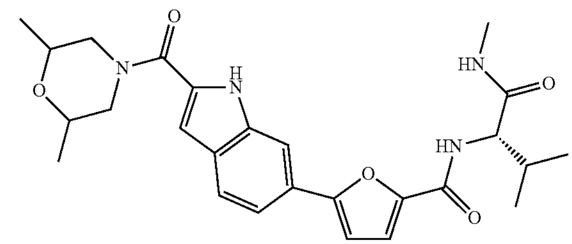 | 5-[2-(2,6-Dimethyl-morpholine-4-carbonyl)-1H-indol-6-yl]-furan-2-carboxylic acid ((S)-2-methyl-1-methylcarbamoyl-propyl)-amide |
| | 5-[2-(Morpholine-4-carbonyl)-1H-indol-6-yl]-furan-2-carboxylic acid (S)-2-methyl-1-methylcarbamoyl-propyl)-amide |
| 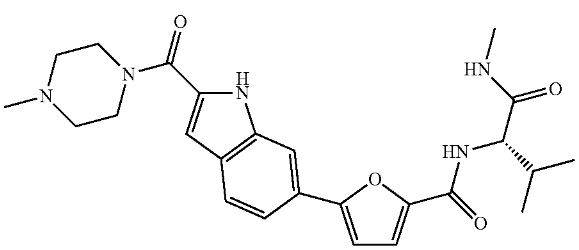 | 5-[2-(4-Methyl-piperazine-1-carbonyl)-1H-indol-6-yl]-furan-2-carboxylic acid ((S)-2-methyl-1-methylcarbamoyl-propyl)-amide |
| | 5-[2-(1,1-Dioxo-□⁶-1-thiomorpholine-4-carbonyl)-1H-indol-6-yl]-furan-2-carboxylic acid ((S)-2-methyl-1-methylcarbamoyl-propyl)-amide |
| 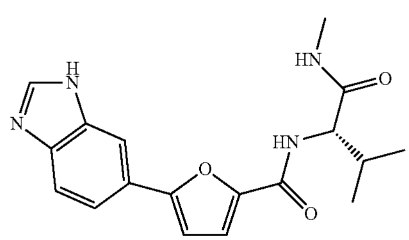 | 5-(3H-Benzimidazol-5-yl)-furan-2-carboxylic acid ((S)-2-methyl-1-methylcarbamoyl-propyl)-amide |
| 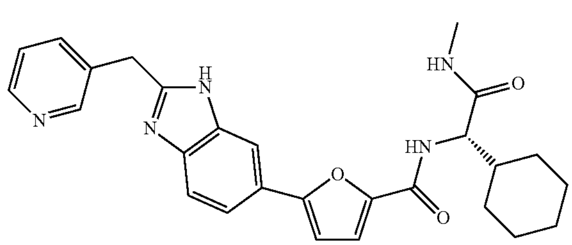 | 5-(2-Pyridin-3-ylmethyl-3H-benzimidazol-5-yl)-furan-2-carboxylic acid ((S)-cyclohexyl-methylcarbamoyl-methyl)-amide |

TABLE I-continued

| Structure | Name |
|---|---|
| 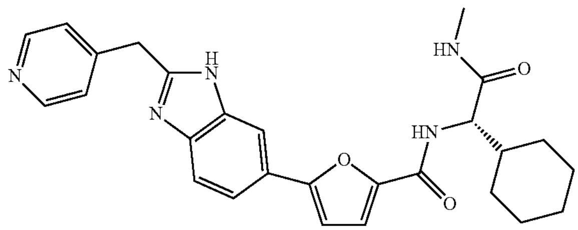 | 5-(2-Pyridin-4-ylmethyl-3H-benzimidazol-5-yl)-furan-2-carboxylic acid ((S)-cyclohexyl-methylcarbamoyl-methyl)-amide |
| 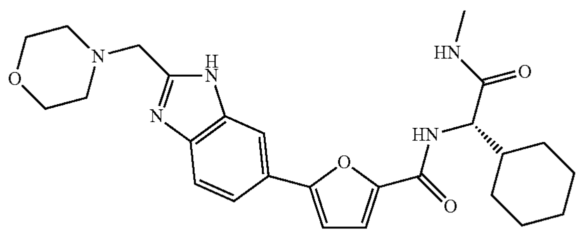 | 5-(2-Morpholin-4-ylmethyl-3H-benzimidazol-5-yl)-furan-2-carboxylic acid ((S)-cyclohexyl-methylcarbamoyl-methyl)-amide |
|  | 5-[2-(2-Oxo-pyrrolidin-1-ylmethyl)-3H-benzimidazol-5-yl]-furan-2-carboxylic acid ((S)-cyclohexyl-methylcarbamoyl-methyl)-amide | or a pharmaceutically acceptable salt thereof.

The following are preferred MMP-13 inhibitors:

TABLE II

| Name | MMP13 IC50 Nm |
|---|---|
| 5-(1H-Indol-6-yl)-furan-2-carboxylic acid ((S)-cyclohexyl-methylcarbamoyl-methyl)-amide | 290 |
| 5-(3H-Benzimidazol-5-yl)-furan-2-carboxylic acid ((S)-cyclohexyl-methylcarbamoyl-methyl)-amide | 270 |
| 5-[2-(Morpholine-4-carbonyl)-1H-indol-6-yl]-furan-2-carboxylic acid ((S)-cyclohexyl-methylcarbamoyl-methyl)-amide | 340 |
| 5-(1H-Pyrrolo[3,2-c]pyridin-6-yl)-furan-2-carboxylic acid ((S)-cyclohexyl-methylcarbamoyl-methyl)-amide | 103 |
| 5-[2-(2,6-Dimethyl-morpholine-4-carbonyl)-1H-indol-6-yl]-furan-2-carboxylic acid ((S)-2-methyl-1-methylcarbamoyl-propyl)-amide | 65 |
| 5-[2-(Morpholine-4-carbonyl)-1H-indol-6-yl]-furan-2-carboxylic acid ((S)-2-methyl-1-methylcarbamoyl-propyl)-amide | 415 |
| 5-[2-(4-Methyl-piperazine-1-carbonyl)-1H-indol-6-yl]-furan-2-carboxylic acid ((S)-2-methyl-1-methylcarbamoyl-propyl)-amide | 300 |
| 5-[2-(1,1-Dioxo-D6-1-thiomorpholine-4-carbonyl)-1H-indol-6-yl]-furan-2-carboxylic acid ((S)-2-methyl-1-methylcarbamoyl-propyl)-amide | 200 |
| 5-(2-Pyridin-4-ylmethyl-3H-benzimidazol-5-yl)-furan-2-carboxylic acid ((S)-cyclohexyl-methylcarbamoyl-methyl)-amide | 34 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example azatidinyl, furanyl, pyranyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, tetrazolyl, pyrrolyl, pyrrolidinyl, pyrrolidinone, imidazolyl, thienyl, thiadiazolyl, oxadiazolyl, thiomorpholinyl, 1,1-dioxo-$1\lambda^6$-thiomorpholinyl, morpholinyl, pyridinyl, pyridinone, 1-oxy-pyridinyl, pyrimidinyl, pyridazinyl, pyrazinyl, pyrrolidinyl, piperidinyl, piperazinyl, quinolinyl, isoquinolinyl, indolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" (or acyl) refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl (or any term using an "alk" or "alkyl" prefix), carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C1-C4 alkyl)-4+ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all Schemes, unless specified otherwise, $R^1$, $R^2$, $R^3$, $R^4$, Ar, W and X in the formulas below shall have the meaning of $R^1$, $R^2$, $R^3$, $R^4$, Ar, W and X in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The appropriately substituted starting materials and intermediates used in the preparation of compounds of the invention are either commercially available or readily prepared by methods known in the literature to those skilled in the art, and are illustrated in the synthetic examples below.

Compounds of Formula (I) may be synthesized by methods outlined in Schemes 1-4.

As illustrated in scheme 1, reaction of a bromoacid of formula (II) with an amine of formula (III) under standard coupling reaction conditions, provides a bromo amide of formula (IV). Reaction of the intermediate of formula (IV) with a boronic acid of formula (V), wherein PG is a protecting group such as BOC, under Suzuki coupling reaction conditions, in a suitable solvent, in the presence of a suitable base and catalyst, provides a compound of Formula (I).

Compounds of Formula (I) may also be prepared by the method outlined in Scheme 2.

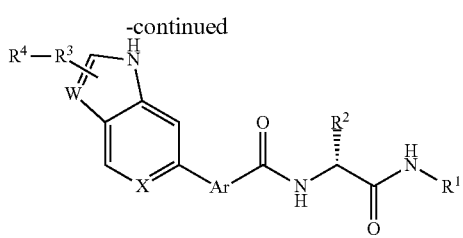

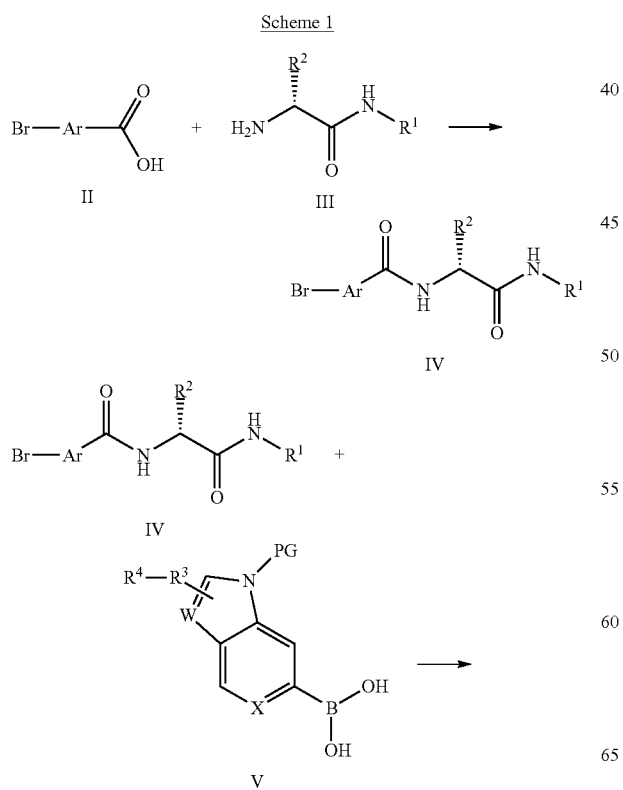

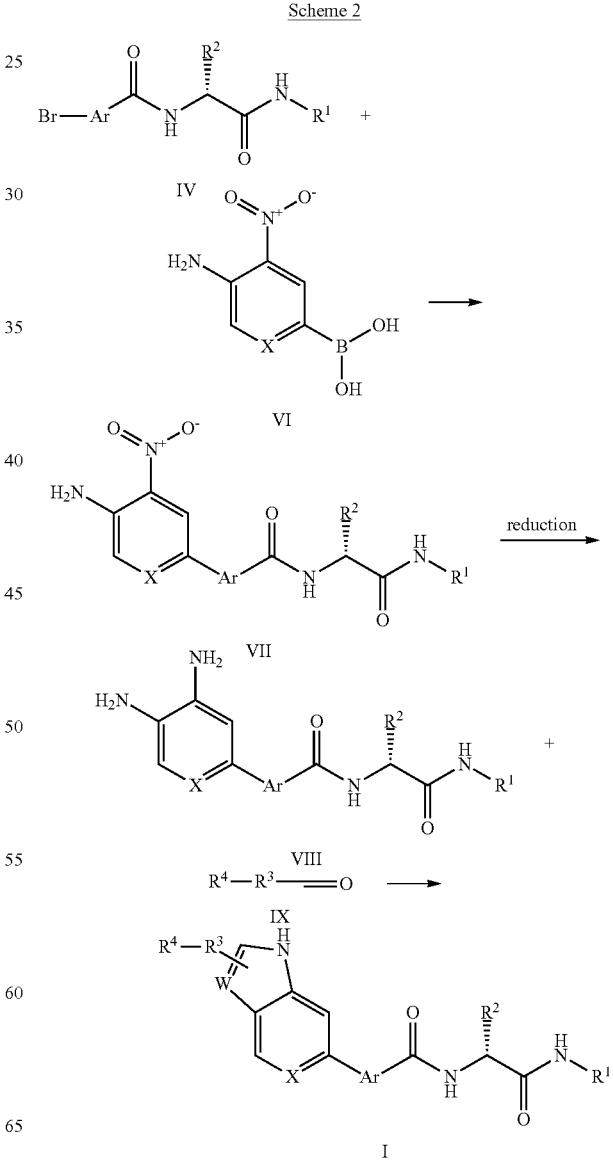

As shown in scheme 2, reaction of the intermediate of formula (IV) with a boronic acid of formula (VI) under Suzuki coupling reaction conditions, in a suitable solvent, in the presence of a suitable base and catalyst, provides a nitro compound of formula (VII). Reduction of the nitro group of the intermediate under standard hydrogenation conditions, using a catalyst such as Raney nickel, provides a diamine of formula (VIII). Reaction of the intermediate of formula (VIII) with an aldehyde of formula (IX), in a suitable solvent, at a suitable temperature, in the presence of a reagent such as sodium bisulfite, provides a compound of Formula (I).

Compounds of Formula (I) may also be made by the method shown in Scheme 3.

Scheme 3

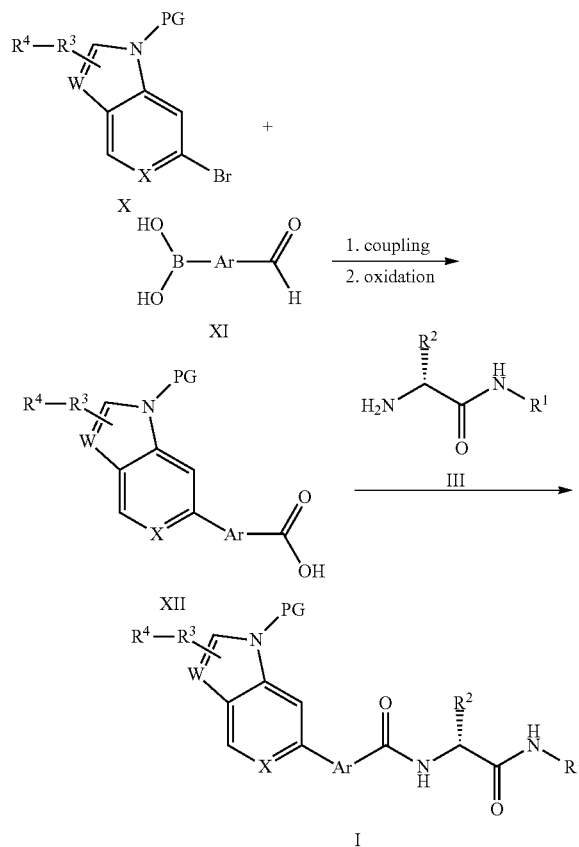

Reaction of a halide of formula (X) with a boronic acid of formula (XI), wherein PG is a protecting group such as BOC, under standard Suzuki coupling reaction conditions, provides the corresponding coupled product. Oxidation of this coupled product, in a suitable solvent, with a suitable reagent, provides the corresponding acid of formula (XII). Reaction of the acid of formula (XII) with an amine of formula (III) under standard coupling reaction conditions, provides a compound of Formula (I).

Compounds of Formula (I) may be synthesized by the method shown in Scheme 4.

Scheme 4

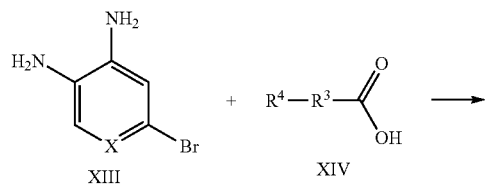

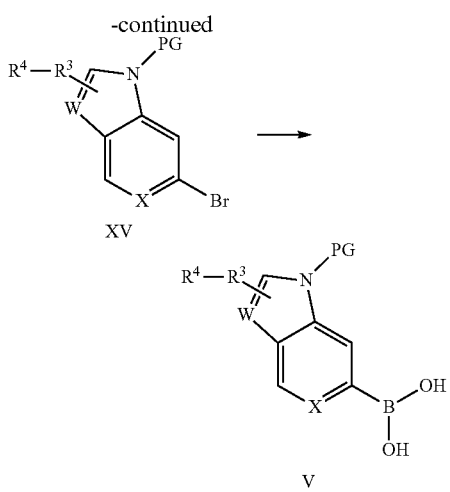

Reaction of diamino compound of formula (XIII) with an acid of formula (XIV), in a suitable solvent, at a suitable temperature, provides a compound of formula (XV). The bromo intermediate of formula (XV) may be converted to the corresponding boronic acid, under standard conditions, to provide an intermediate boronic acid of formula (V) which may be converted to a compound of Formula (I) using the method shown in scheme 1.

Further modification of the initial product of Formula (I) by methods known in the art and illustrated in the Examples below, may be used to prepare additional compounds of this invention.

EXAMPLES

Example 1

5-(1H-Indol-6-yl)-furan-2-carboxylic acid ((S)-cyclohexyl-methylcarbamoyl-methyl)-amide

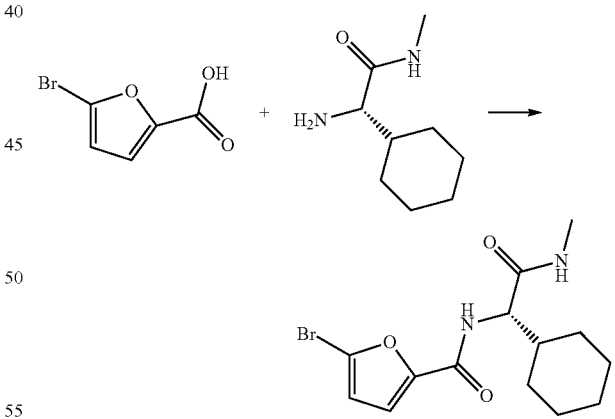

5-Bromo-furan-2-carboxylic acid ((S)-cyclohexyl-methylcarbamoyl-methyl)-amide

5-Bromo-furan-2-carboxylic acid (2.0 g, 10.4 mmol) is dissolved in DMF (25 mL) and then O-(7-azabenzotriazol-1-yl)-N,N,N',N'-tetramethyluronium hexafluorophosphate (HATU) (4.3 g, 11.5 mmol), N,N-diisopropylethylamine (DIEA) (5.8 mL, 31 mmol) and (S)-2-Amino-2-cyclohexyl-N-methyl-acetamide hydrochloride (2.97 g, 10.4 mmol) are added. The reaction is stirred at room temperature overnight. After 16 hours, the reaction is quenched with water, and the product extracted with ethyl acetate. The EtOAc layer is filtrated and the solid is dried in vacuo to give a beige solid. 2.8 g, 78% LC/MS ESI m/z (M+H)+=343.3

5-Bromo-furan-2-carboxylic acid ((S)-2-methyl-1-methylcarbamoyl-propyl)-amide LC/MS ESI m/z (M+H)+= 303.28 was prepared in the same fashion.

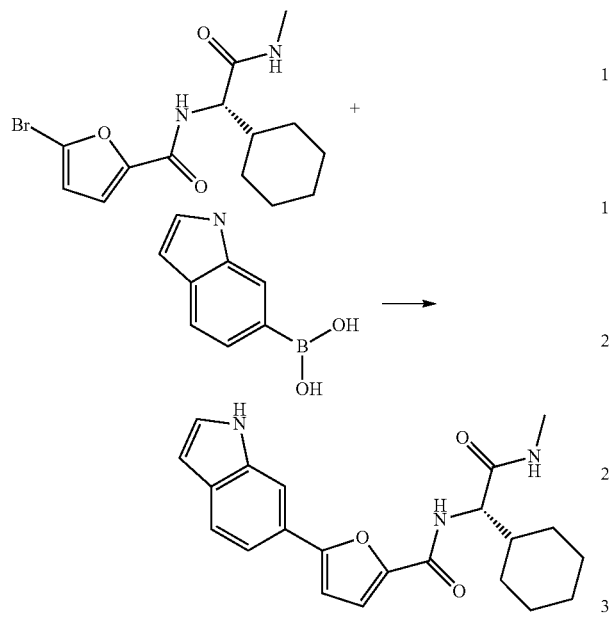

5-(1H-Indol-6-yl)-furan-2-carboxylic acid ((S)-cyclohexyl-methylcarbamoyl-methyl)-amide In a pressure vial 5-Bromo-furan-2-carboxylic acid ((S)-cyclohexyl-methylcarbamoyl-methyl)-amide (190 mg, 0.55 mmol), indole-6-boronic acid (106 mg, 0.66 mmol), and bis (di-tert-butyl(4-dimethylaminophenyl)phosphine)dichloropalladium(II) (39 mg, 0.05 mmol) are dissolved in DMF (3 mL). A 2M sodium carbonate solution (3.0 mL) is added and the resulting solution is degassed with Argon during 5 min. The vessel was heated at 100° C. for 20 min in the Microwave. Upon cooling the resulting mixture is diluted with EtOAc/H$_2$O and the aqueous phase is extracted with EtOAc. The combined organic extracts are washed with brine, dried over MgSO$_4$, and the solvent is evaporated. The residue is purified using reversed phase (HPLC). 137 mg, 65% LC/MS ESI m/z (M+H)+=380.5.

Example 2

5-[2-(2,5-Dimethyl-2H-pyrazol-3-yl)-3H-benzimidazol-5-yl]-furan-2-carboxylic acid ((S)-cyclohexyl-methylcarbamoyl-methyl)-amide

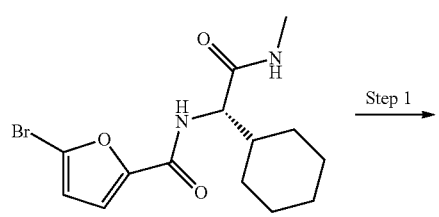

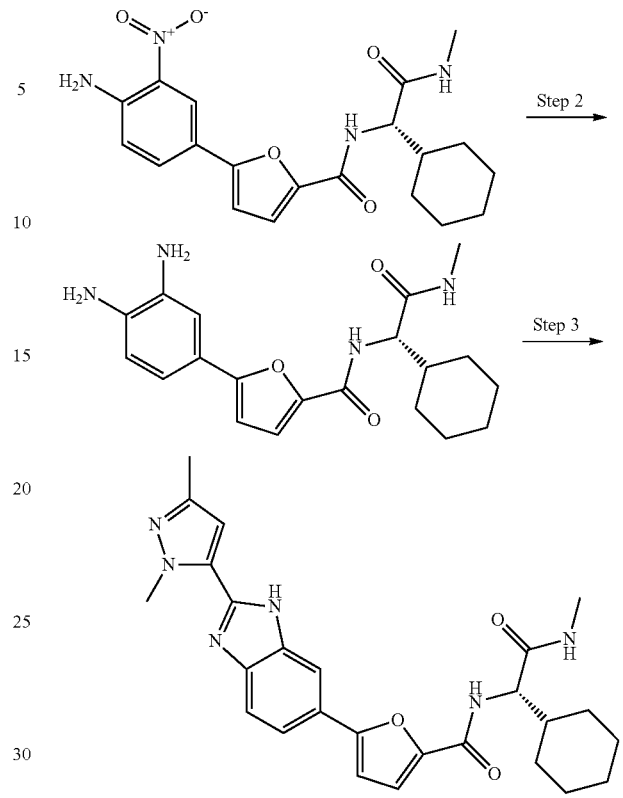

Step 1:

5-Bromo-furan-2-carboxylic acid ((S)-cyclohexyl-methylcarbamoyl-methyl)-amide (0.50 g, 1.46 mmol), 4-amino-3-nitrophenylboronic acid pinacol ester (0.54 g, 2.04 mmol) and tetrakis(triphenylphosphine)palladium (0.17 g, 0.15 mmol) are dissolved in DME (50 mL). A 2M sodium carbonate solution (2.9 mL, 5.83 mmol) is added and the resulting solution is degassed with Argon during 5 min. The solution is heated to reflux (100° C.) for 4 h under Argon. Upon cooling the resulting mixture is diluted with EtOAc/H$_2$O and the aqueous phase is extracted with EtOAc. The yellow product is precipitating out of the organic layer and is filtered off. The product is washed with EtOAc and dried in vacuum. 493 mg, 85% LC/MS ESI m/z (M+H)+=401.42.

Step 2:

To a solution of 5-(4-amino-3-nitro-phenyl)-furan-2-carboxylic acid ((S)-cyclohexyl-methylcarbamoyl-methyl)-amide (493 mg, 1.23 mmol) in ethanol (25 mL) is added Raney-Nickel (50 mg, slurry in water). The mixture is stirred under a hydrogen atmosphere for 16 h. The mixture is filtered through Celite and the solvent is evaporated. The product is washed with cold MeOH to give a white solid. 308 mg, 68%, LC/MS ESI m/z (M+H)+=371.36.

Step 3:

5-(3,4-Diamino-phenyl)-furan-2-carboxylic acid ((S)-cyclohexyl-methylcarbamoyl-methyl)-amide (25 mg, 67 mmol), 1,3-dimethyl-1H-pyrazole-4-carbaldehyde (9.2 mg, 74 mmol), and sodium bisulfite (7.73 mg, 74 mmol) are dissolved in DMF (1 mL) and the mixture is heated at 130° C. for 12 h. The mixture is filtered and purified on reversed phase (HPLC). The product is obtained as a beige solid. 4.2 mg, 13%, LC/MS ESI m/z (M+H)+=476.54.

Example 3

5-(2-Pyridin-4-ylmethyl-3H-benzimidazol-5-yl)-furan-2-carboxylic acid ((S)-cyclohexyl-methylcarbamoyl-methyl)-amide

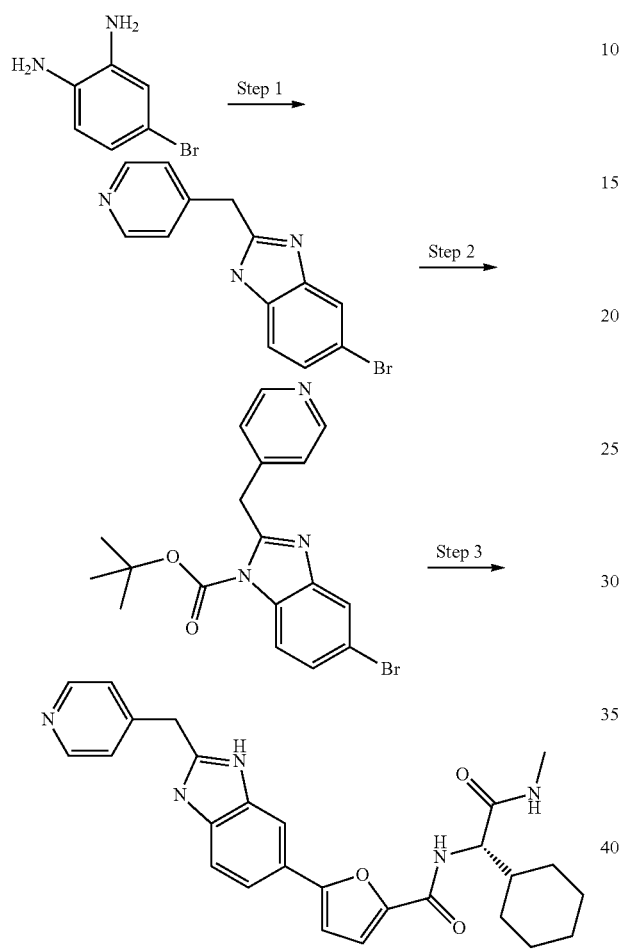

Step 1:
4-Bromo-benzene-1,2-diamine (0.50 g, 2.67 mmol) and pyridin-4-yl-acetic acid (0.46 g, 2.67 mmol) are suspended in polyphosphoric acid (5 mL). The mixture is heated at 185° C. for 2 h. After cooling to room temperature the mixture is diluted with water followed by addition of concentrated ammonia (pH=10). The mixture is extracted with EtOAc and the organic layer is washed with brine and dried over MgSO$_4$. After removal of the solvent the product is obtained as a red oil. 512 mg, 67%.

Step 2:
To a solution of 5-bromo-2-pyridin-4-ylmethyl-1H-benzimidazole (512 mg, 1.78 mmol) in acetonitrile (20 mL) is added 4-dimethylaminopyridine (22 mg, 0.178 mmol) followed by Boc anhydride (465 mg, 2.113 mmol). The mixture is stirred for 12 h at room temperature. After dilution with EtOAc the mixture is extracted with water. The organic layer is washed with brine, dried over MgSO4, and the solvent is removed in vacuo. 670 mg, 97%.

Step 3:
A pressure vial is charged with 5-bromo-2-pyridin-4-ylmethyl-1H-benzimidazole-1-carboxylic acid tert-butyl ester (100 mg, 0.26 mmol), bis(pinacolato)diboron (72 mg, 0.28 mmol), KOAc (99 mg, 1.01 mmol), and [1,1'-bis(diphenylphosphino)ferrocene]dichloropalladium(II) complex with dichloromethane (1:1) (PdCl$_2$(dppf)*CH$_2$Cl$_2$) (8.2 mg, 0.01 mmol). After flushing with nitrogen, DME (2 mL) is added and the reaction stirred at 100° C. for 2 h. The mixture is cooled to room temperature before 5-bromo-furan-2-carboxylic acid ((S)-cyclohexyl-methylcarbamoyl-methyl)-amide (88 mg, 0.26 mmol), PdCl$_2$(dppf)*CH$_2$Cl$_2$ (8.2 mg, 0.01 mmol), and 2M Na$_2$CO$_3$ solution (0.84 mL, 1.68 mmol) are added. The mixture is stirred at 110° C. for 8 h. Water is added and the mixture is extracted with EtOAc. The organic layer was washed with brine and dried over MgSO$_4$. After removal of the solvent, the residue was purified by reversed phase (HPLC). The product is obtained as a pale yellow solid. 19 mg, 15%, LC/MS ESI m/z (M+H)+=472.46

The following compounds are prepared according to this procedure (in case of commercially available 5-bromo-benzimidazoles or 6-bromoindoles from step 2):

5-(3H-Benzimidazol-5-yl)-furan-2-carboxylic acid ((S)-cyclohexyl-methylcarbamoyl-methyl)-amide LC/MS ESI m/z (M+H)+=381.39

5-(2-Amino-3H-benzimidazol-5-yl)-furan-2-carboxylic acid ((S)-cyclohexyl-methylcarbamoyl-methyl)-amide LC/MS ESI m/z (M+H)+=396.40

5-(2-Pyridin-3-ylmethyl-3H-benzimidazol-5-yl)-furan-2-carboxylic acid ((S)-cyclohexyl-methylcarbamoyl-methyl)-amide LC/MS ESI m/z (M+H)+=472.46

5-(2-Morpholin-4-ylmethyl-3H-benzimidazol-5-yl)-furan-2-carboxylic acid ((S)-cyclohexyl-methylcarbamoyl-methyl)-amide LC/MS ESI m/z (M+H)+=481.57

5-[2-(2-Oxo-pyrrolidin-1-ylmethyl)-3H-benzimidazol-5-yl]-furan-2-carboxylic acid ((S)-cyclohexyl-methylcarbamoyl-methyl)-amide LC/MS ESI m/z (M+H)+=479.56

Example 4

5-(2-Acetylamino-3H-benzimidazol-5-yl)-furan-2-carboxylic acid ((S)-cyclohexyl-methylcarbamoyl-methyl)-amide

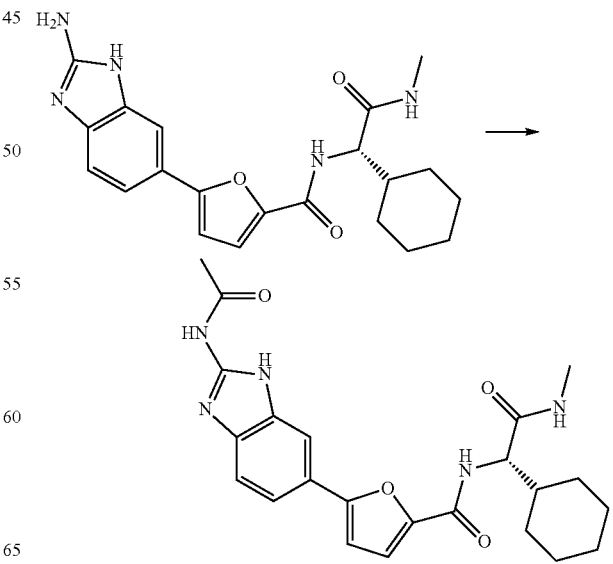

To a solution of 5-(2-amino-3H-benzimidazol-5-yl)-furan-2-carboxylic acid ((S)-cyclohexyl-methylcarbamoyl-methyl)-amide (10 mg, 0.025 mmol) in anhydrous pyridine (1 mL) is added acetic anhydride. The mixture is heated at 100° C. for 2 h. After cooling to room temperature the mixture is purified by reversed phase (HPLC). 4.6 mg, 42%, LC/MS ESI m/z (M+H)+=438.47.

Example 5

5-[2-(Morpholine-4-carbonyl)-1H-indol-6-yl]-furan-2-carboxylic acid ((S)-cyclohexyl-methylcarbamoyl-methyl)-amide

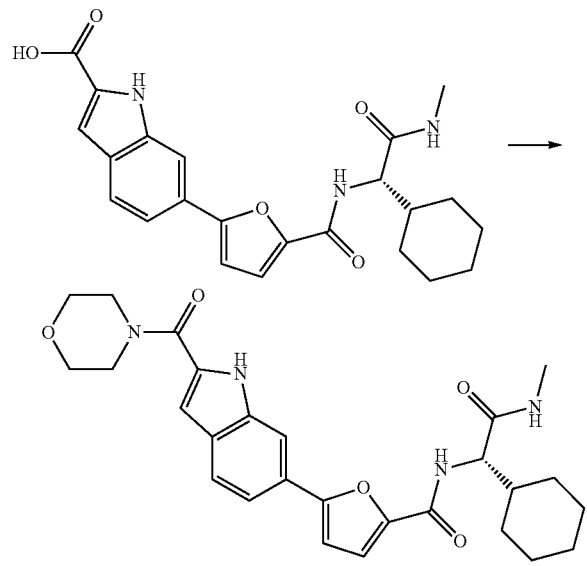

To a solution of 6-{5-[((S)-cyclohexyl-methylcarbamoyl-methyl)-carbamoyl]-furan-2-yl}-1H-indole-2-carboxylic acid (20 mg, 0.047 mmol) is added subsequently HATU (10 mg, 0.052 mmol), DIEA (0.026 mL, 0.142 mmol), and morpholine (4.5 mg, 0.052 mmol). The reaction is stirred at room temperature for 2 h and is directly purified by reversed phase (HPLC). 7.0 mg, 30%, LC/MS ESI m/z (M+H)+=493.43.

The following compounds are prepared according to this procedure:

6-{5-[((S)-Cyclohexyl-methylcarbamoyl-methyl)-carbamoyl]-furan-2-yl}-1H-indole-2-carboxylic acid methylamide LC/MS ESI m/z (M+H)+=437.38

6-{5-[((S)-Cyclohexyl-methylcarbamoyl-methyl)-carbamoyl]-furan-2-yl}-1H-indole-2-carboxylic acid dimethylamide LC/MS ESI m/z (M+H)+=451.40

5-[2-(2,6-Dimethyl-morpholine-4-carbonyl)-1H-indol-6-yl]-furan-2-carboxylic acid ((S)-2-methyl-1-methylcarbamoyl-propyl)-amide LC/MS ESI m/z (M+H)+=481.47

5-[2-(Morpholine-4-carbonyl)-1H-indol-6-yl]-furan-2-carboxylic acid ((S)-2-methyl-1-methylcarbamoyl-propyl)-amide LC/MS ESI m/z (M+H)+=453.43

5-[2-(4-Methyl-piperazine-1-carbonyl)-1H-indol-6-yl]-furan-2-carboxylic acid ((S)-2-methyl-1-methylcarbamoyl-propyl)-amide LC/MS ESI m/z (M+H)+=466.51

5-[2-(1,1-Dioxo-$\lambda^6$-1-thiomorpholine-4-carbonyl)-1H-indol-6-yl]-furan-2-carboxylic acid ((S)-2-methyl-1-methylcarbamoyl-propyl)-amide LC/MS ESI m/z (M+H)+=501.42

Example 6

5-(1H-Pyrrolo[3,2-c]pyridin-6-yl)-furan-2-carboxylic acid ((S)-cyclohexyl-methylcarbamoyl-methyl)-amide

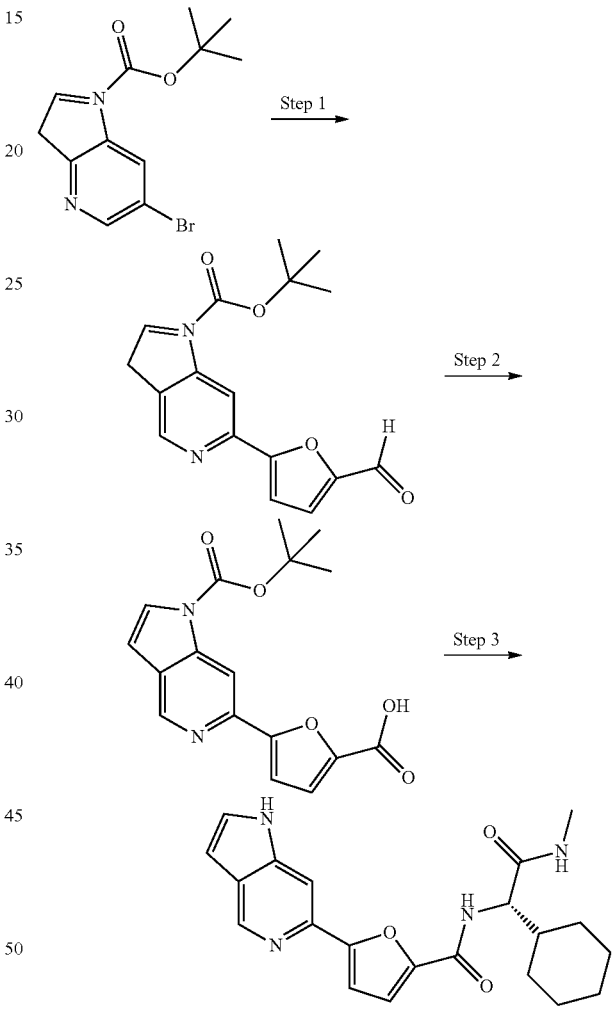

Step 1:

6-Bromo-pyrrolo[3,2-c]pyridine-1-carboxylic acid tert-butyl ester (0.75 g, 2.53 mmol), 2-furaldehyde 4-boronic acid (1.06 g, 7.59 mmol), and tetrakis(triphenylphosphine)palladium (0.29 g, 0.25 mmol) are dissolved in DME (13 mL). A 2M sodium carbonate solution (3.2 mL, 6.32 mmo) is added and the resulting solution is degassed with Argon during 5 min. The solution is heated to reflux (94° C.) overnight under Argon. Upon cooling the resulting mixture is diluted with EtOAc/H$_2$O and the aqueous phase is extracted with EtOAc. The combined organic extracts are washed with brine, dried over MgSO$_4$, and the solvent is evaporated. The residue is purified using reversed phase (HPLC). 162 mg, 21%

Step 2:

To a solution of 6-(5-Formyl-furan-2-yl)-pyrrolo[3,2-c]pyridine-1-carboxylic acid tert-butyl ester (162 mg, 0.52 mmol) in dioxane (5 mL) is added sodium phosphate (monobasic, 279 mg, 2.02 mmol) in water (5 mL) followed by sulfamic acid (76 mg, 0.78 mmol). The reaction mixture is cooled to 0° C. before sodium chlorite (117 mg, 80%, 1.04 mmol) in water (5 mL) is added over a 10 minutes period at 0° C. The ice bath is removed and the solution is stirred for 30 minutes. Sodium sulfite (117 mg, 0.93 mmol) is added and stirred for 30 minutes. The reaction mixture is acidified with 2 N HCl (pH=4) and extracted with EtOAc (2×25 mL). The combined organic layers are washed with brine, dried over $MgSO_4$, and the solvent is evaporated. The product is obtained as a dark yellow-brownish solid 164 mg, 96%

Step 3:

6-(5-Carboxy-furan-2-yl)-pyrrolo[3,2-c]pyridine-1-carboxylic acid tert-butyl ester (164 mg, 0.50 mmol) is dissolved in DMF (5 mL) and O-(benzotriazol-1-yl)-N,N,N',N'-tetramethyluronium tetrafluoroborate (TBTU) (955 mg, 2.50 mmol), DIEA (0.55 mL, 3.00 mmol) is added as well as the amino acid (284 mg, 1.00 mmol). The reaction is capped and stirred at room temperature. After 5 hours, the reaction is quenched with water and extracted with EtOAc. The organic layer is washed with brine, dried over $MgSO_4$, and the solvent is evaporated. The crude material is purified on reversed phase (HPLC). The product was obtained as a white solid 16 mg, 8%. LC/MS ESI m/z (M+H)+=381.70.

Assessment of Biological Properties

The biological properties of the compounds of the formula I can be assessed using the assays described below in addition to other art recognized assays.

The EnzoLyte™ 520 Generic MMP Assay Kit (AnaSpec Inc.) can detect the activity of several MMPs including MMP-1, 2, 3, 7, 8, 9, 13, and 14. This kit uses a 5-FAM/QXL™ 520 fluorescence resonance energy transfer (FRET) peptide as an MMP substrate. In the intact FRET peptide, the fluorescence of 5-FAM is quenched by QXL™ 520. Upon cleavage into two separate fragments by MMPs, the fluorescence of 5-FAM is recovered, and can be monitored at excitation/emission wavelengths=490 nm/520 nm. The assays are performed in a convenient 96-well or 384-well microplate format.

Preferred compounds will have an IC50 of <500 nM.

Therapeutic Use

As can be demonstrated by the assays described above, the compounds of the invention are useful in inhibiting MMP-13. Compounds of formula I are therefore useful in the treatment of diseases including rheumatoid arthritis, osteoarthritis, osteoporosis, peridontitis, atherosclerosis, congestive heart failure, multiple sclerosis and tumor metastasis. They can be used in patients as drugs, particularly in the form of pharmaceutical compositions as set forth herein. As mentioned previously, MMP-13 are thought to play a major role on extracellular matrix degradation and cellular processes such as proliferation, migration (adhesion/dispersion), differentiation, angiogenesis, apoptosis and host defense, compounds of formula I are therefore also useful in the treatment of the following diseases:

contact dermatitis, bone resorption diseases, reperfusion injury, asthma, Guillain-Barre syndrome, Crohn's disease, ulcerative colitis, psoriasis, graft versus host disease, systemic lupus erythematosus and insulin-dependent diabetes mellitus, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopheresis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure.

As disclosed in the Background of the Invention, the compounds of the invention will be useful for treating tumor metastasis. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I):

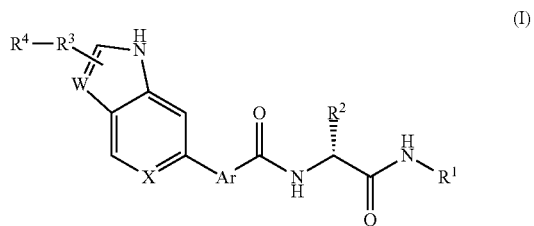

wherein:
$R^1$ is $C_1$-$C_5$ alkyl optionally substituted with 1-2 substituents chosen from hydroxyl, $C_1$-$C_5$ alkoxy, aryl and heteroaryl;
$R^2$ is $C_1$-$C_5$ alkyl, carbocycle, heterocycle or heteroaryl, each optionally independently substituted with 1-2 substituents chosen from amino, hydroxyl and $C_1$-$C_5$ alkoxy;
$R^3$ is a bond, —(CH$_2$)$_n$—, —C(O)—, O, NH or —S(O)$_m$—;
$R^4$ is hydrogen, $C_1$-$C_5$ alkyl, amino, alkylamino, dialkylamino, heterocyclyl or heteroaryl, each optionally independently substituted with 1-3 substituents chosen from $C_1$-$C_5$ alkyl, acyl, halogen, hydroxyl, oxo and $C_1$-$C_5$ alkoxy;
W is N, O or CH wherein CH is optionally substituted with halogen, $C_1$-$C_5$ alkyl, $C_1$-$C_5$ alkoxy or —C(O)—NH$_2$ wherein the nitrogen atom is optionally mono or di substituted with a $C_1$-$C_3$ alkyl group;
X is N or CH;
Ar is a heteroaryl ring chosen from furanyl, thiazolyl, pyrazolyl, imidazolyl, pyrrolyl, pyridinyl, pyrimidinyl, pyridazinyl and quinolinyl;
each m, n is 0-2;
wherein each $R^1$-$R^4$ is optionally partially or fully halogenated;
or a pharmaceutically acceptable salt thereof.

2. The compound according to claim 1, and wherein
$R^1$ is $C_1$-$C_5$ alkyl optionally substituted with 1-2 substituents chosen from hydroxyl and $C_1$-$C_5$ alkoxy;
$R^2$ is $C_1$-$C_5$ alkyl, cyclobutyl, cyclopentyl, cyclohexyl, tetrahydropyranyl, piperidinyl or piperazinyl, each optionally independently substituted with 1-2 substituents chosen from amino, hydroxyl and $C_1$-$C_5$ alkoxy;
$R^3$ is a bond, CH$_2$, O, NH, —C(O)—, —S(O)$_m$— or —SO$_2$—;
$R^4$ is hydrogen, $C_1$-$C_5$ alkyl, amino, alkylamino, dialkylamino, morpholinyl, thiomorpholinyl, 1,1-dioxo-1$\lambda^6$-thiomorpholinyl, piperazinyl, piperidinyl, pyrazolyl, imidazolyl, pyrrolyl, pyrrolidinyl or pyridinyl, each optionally independently substituted with 1-3 substituents chosen from $C_1$-$C_5$ alkyl, acyl, halogen, hydroxyl, oxo and $C_1$-$C_5$ alkoxy;
W is N, O or CH;
X is N or CH;
Ar is a heteroaryl ring chosen from furanyl, thiazolyl, pyrazolyl, imidazolyl, pyrrolyl, pyridinyl, pyrimidinyl and pyridazinyl.

3. The compound according to claim 2 and wherein
$R^1$ is $C_1$-$C_5$ alkyl;
$R^2$ is $C_1$-$C_5$ alkyl or cyclohexyl;
$R^3$ is CH$_2$ or —C(O)—;

R[4] is hydrogen, morpholinyl, thiomorpholinyl, 1,1-dioxo-1λ[6]-thiomorpholinyl, piperazinyl, piperidinyl, pyrazolyl or pyridinyl, each optionally independently substituted with 1-3 substituents $C_1$-$C_5$ alkyl;

W is N or CH;

Ar is furanyl.

4. The compound according to claim 3 and wherein

R[1] is methyl;

R[2] is isopropyl or cyclohexyl;

R[3] is $CH_2$ or —C(O)—;

R[4] is hydrogen, morpholinyl or pyridinyl, each optionally substituted with 1-3 methyl groups.

5. The compound according to claim 4 and wherein

X is CH.

6. The compound according to claim 4 and wherein

X is N.

7. A compound chosen from

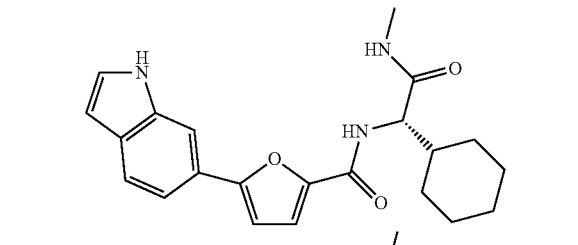

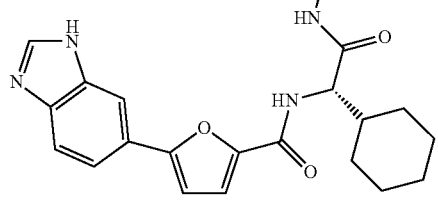

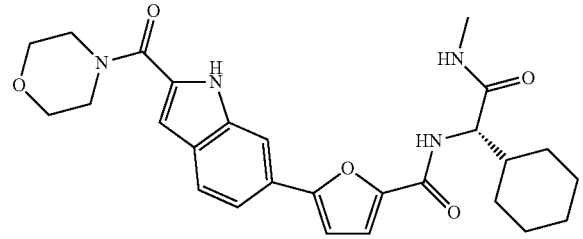

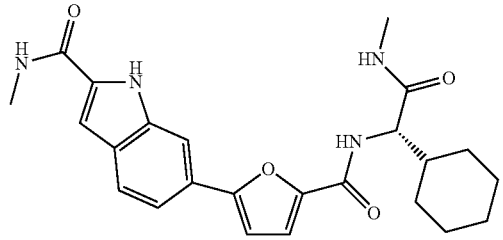

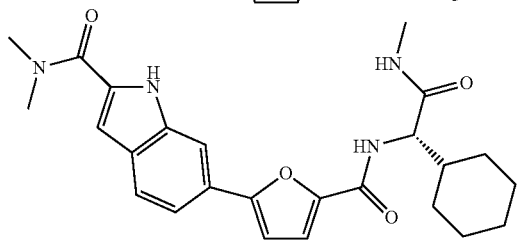

-continued

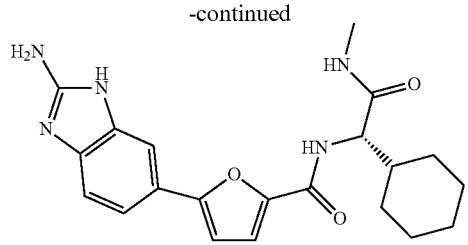

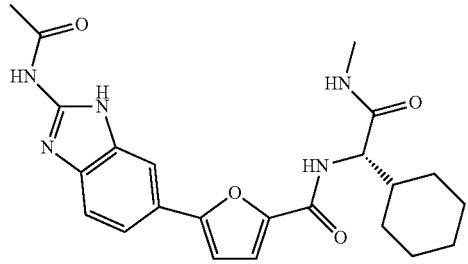

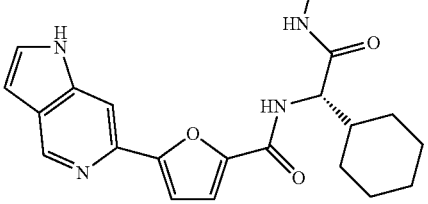

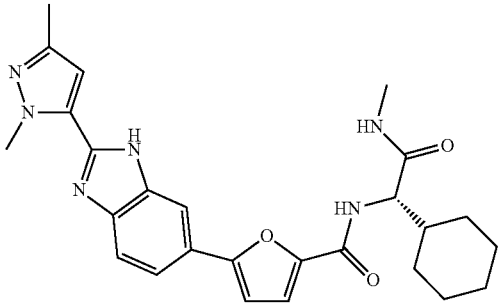

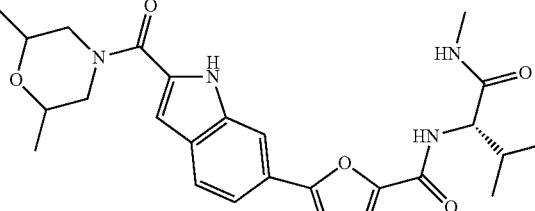

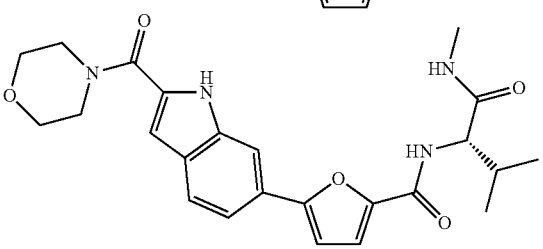

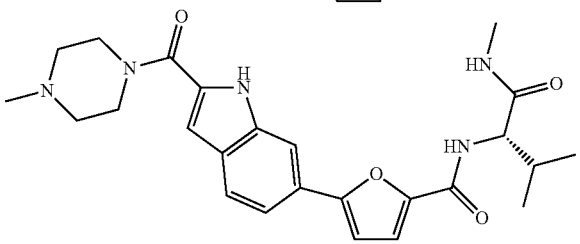

29

-continued

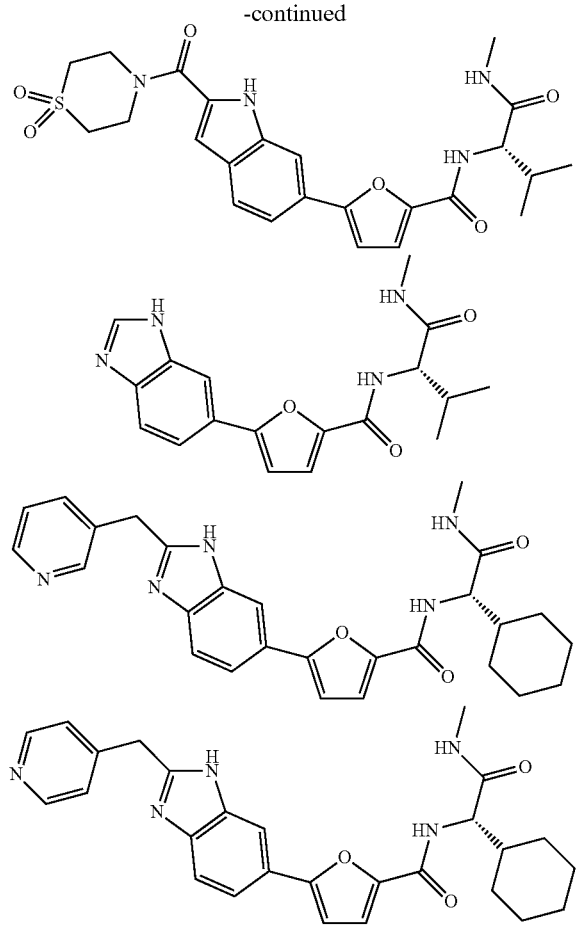

30

-continued

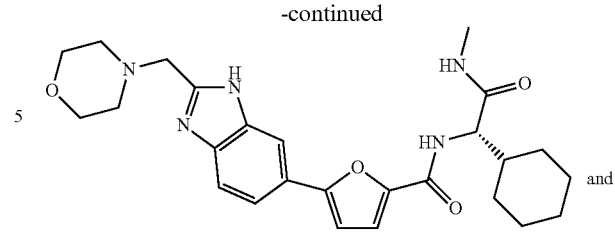

and

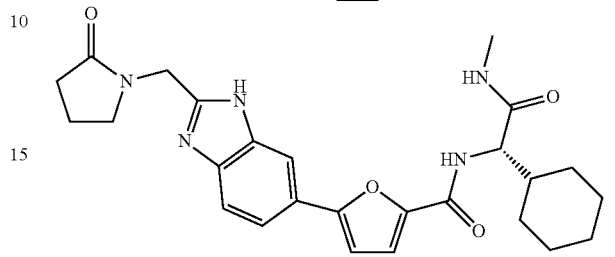

or a pharmaceutically acceptable salt thereof.

8. A pharmaceutical composition comprising a therapeutically effective amount of a compound according to claim 1 and one or more pharmaceutically acceptable carriers and/or adjuvants.

9. A method of treating a disease selected from rheumatoid arthritis, osteoarthritis, osteoporosis, periodontitis, atherosclerosis, congestive heart failure, and breast cancer comprising administering a therapeutically effective amount of a compound according to claim 1.

* * * * *